(12) United States Patent
Dueholm

(10) Patent No.: US 6,885,198 B2
(45) Date of Patent: Apr. 26, 2005

(54) METHOD AND DEVICE FOR TESTING A MAT MADE OF BIOMASS PARTICLES

(75) Inventor: Sten Dueholm, Hellerup (DK)

(73) Assignee: Dieffenbacher GmbH + Co. KG, Eppingen (DE)

(*) Notice: Subject to any disclaimer, the term of this patent is extended or adjusted under 35 U.S.C. 154(b) by 0 days.

(21) Appl. No.: 10/315,226

(22) Filed: Dec. 10, 2002

(65) Prior Publication Data

US 2003/0137288 A1 Jul. 24, 2003

(30) Foreign Application Priority Data

Dec. 10, 2001 (DE) ......................................... 101 60 398

(51) Int. Cl.⁷ .............................................. G01R 27/32
(52) U.S. Cl. ..................................................... 324/639
(58) Field of Search ................................ 324/637, 639, 324/644, 71.3; 250/359, 494.1; 378/89, 21

(56) References Cited

U.S. PATENT DOCUMENTS

| | | | | |
|---|---|---|---|---|
| 4,047,036 A | * | 9/1977 | Smith et al. ................... | 378/56 |
| 4,633,420 A | * | 12/1986 | Masanobu ................... | 702/167 |
| 4,720,808 A | * | 1/1988 | Repsch ....................... | 702/175 |
| 5,233,195 A | * | 8/1993 | Hellstrom et al. ........ | 250/360.1 |
| 5,351,203 A | * | 9/1994 | Hoffman et al. ............ | 702/172 |
| 5,687,209 A | * | 11/1997 | Adams ......................... | 378/22 |

FOREIGN PATENT DOCUMENTS

| | | |
|---|---|---|
| CA | 1 202 431 A | 5/1984 |
| DE | 34 29 135 A1 | 2/1986 |
| EP | 0 233 389 A1 | 8/1987 |
| GB | 2 054 841 A | 2/1981 |
| WO | WO 94/27138 A1 | 11/1994 |

OTHER PUBLICATIONS

Patent Abstracts of Japan, vol. 010, No. 097 (P–446), Apr. 15, 1986 & JP 60–230009 (Toshiba KK), Nov. 15, 1985.
Patent Abstracts of Japan, vol. 010, No. 097 (P–446), Apr. 15, 1986 & JP 60–230010 (Toshiba KK), Nov. 15, 1985.
Derek W. Adams et al., "High Resolution Solid State Sensor for Strip Edge Drop and Thickness Profile," Iron and Steel Engineer, Association of Iron and Steel Engineers, Pittsburgh, PA, Bd. 75, Nr. 9, Sep. 1, 1998, pp. 33–36, XP–000788068.
S. Gondrom and S. Schröpfer, FhG ITFP, Saarbrucken, Germany, "Digital computed laminography and tomosynthesis—functional principles and industrial applications," published in NDT.net, vol. 4, No. 7 (Jul. 1999).

* cited by examiner

Primary Examiner—N. Le
Assistant Examiner—Amy He
(74) Attorney, Agent, or Firm—Foley & Lardner LLP

(57) ABSTRACT

A testing device tests a mat that is moved in one direction and that is made of biomass particles for manufacturing boards. On one side of the mat, radiation sources are positioned with a transversely spaced-apart relationship transverse to the direction of motion. On the other side of the mat, a line of detector elements is arranged beneath each of the radiation sources. A fan-shaped beam impinges on said detector elements. The beam passes either through one standard body, through the mat, or through neither the standard body nor the mat and is received by the detector elements and converted into electric output signals. The output signals are transferred via lines to an evaluating circuit that controls a device for removing mat portions that contain unwanted matter or the weight per unit area of which is too low.

37 Claims, 5 Drawing Sheets

METHOD AND DEVICE FOR TESTING A MAT MADE OF BIOMASS PARTICLES

BACKGROUND

Mats to be tested consist of fibers and/or wood chips and are actually preferably formed into chip boards, fiber boards, oriented strand boards ("OSBs") and similar boards in continuous double band presses. Today's current, continuous double band presses are isochoric, i.e., they operate by maintaining a predetermined distance between the press plates. The double band presses are provided with steel belts that run in opposite directions relative to one another and that compress the mat to achieve a final thickness. Foreign matter and zones in the mat that cannot be compressed to this final thickness may cause bulges, cracks or even cuts to be formed in the steel belts and may even damage the roller bar or roller chain systems supporting the steel bands and the heating plates.

To avoid such damage, it has become known in board manufacturing to make use of metal detectors which sense magnetizable and non-magnetizable metal pieces in the mat. Upon detection of such metal pieces, the forming belt, which is divided transverse to the direction of motion, is parted in the direction of motion and the defective portion of mat is evacuated into a discharge chute. After closure of the forming belt, the manufacturing process is carried on with a flaw free mat. Magnetizable metal pieces are also removed from the mat by magnets.

CA 1 202 431 A teaches to dispose, on one side of a plate-shaped product, one radiation source the output beam of which is fan-shaped. The width of the beam extends transverse to the direction of motion of the product. On the other side of the product, detectors are arranged in only one row on an arc of a circle, the center of which is the radiation source. The detectors are mounted in alignment with the fan-shaped beam. A distant positioned detector receives radiation from a radiation source that has not penetrated the product. This distant positioned detector serves to automatically calibrate the known device. This device is intended for determining the weight per unit area of the product. If the density of the product is constant, the thickness may be determined from the weight per unit area. On the other hand, if the thickness of the product is constant, the density of the product may be deduced from the weight per unit area.

SUMMARY

It is the object of the invention to detect, aside from metallic pieces, other foreign matter of undesired high density in the mat and to avoid that this foreign matter is brought into the double band press connected downstream where it may lead to local concentrations of too high density.

The solution to this object is achieved by a method of testing a mat moved in one direction and made of biomass particles, more specifically of fibers and/or wood chips for manufacturing boards, wherein, on a first side of the mat, there is provided an array of detector elements extending transverse to the direction of motion of the mat. The detector elements receive the beam that originates from a second side of the mat located opposite the first side thereof and that has passed through the mat. Each detector element produces electrical output signals that are proportional to the received beam and that these signals are entered into an evaluating circuit. The detector elements are arranged on a plane parallel to the mat. On the second side of the mat, there is provided an array of radiation sources that extends transverse to the direction of motion. The radiation sources are positioned with a transversely spaced-apart relationship transverse to the direction of motion of the mat. The beam originating from every radiation source is shared into a fan-shaped beam, a width of each fan-shaped beam extending transverse to the direction of motion of the mat. The distal ends of neighboring fan-shaped beams are disposed in overlapping relation with one another transverse to the direction of motion of the mat. The overlapping is performed over at least one thickness of the mat. One line of detector elements of the array of detector elements is radiated by each fan-shaped beam. Neighboring fan-shaped beams and the respective one of the associated lines of detector elements are longitudinally spaced a distance from each other in the direction of motion of the mat.

Transmitters are particularly suitable radiation sources. The mat may be tested over the entire surface thereof in this manner. Each detector element may be provided with several detector cells. Depending on the number of detector cells having any degree of resolution, information about the density of the mat is obtained. The optimum number of radiation sources may be used in each case. The spacing between the radiation sources is preferably adjustable. The fan-shaped beams allow for a compact construction and high operational reliability. The overlaps serve on the one hand to reliably acquire data over the entire width of the mat and on the other hand to improve the evaluation of the acquired data. Through the longitudinal spacing it is made certain that the beam of each radiation source only impinges on the corresponding line of detector elements.

According to another embodiment of the invention, values may be calculated normal to the surface of the mat. For example, the various distances between the radiation source and the mat due to the fan-shaped path of the rays, the various beam paths through the mat and the variously radiated surfaces of the detector elements are trigonometrically compensated. Further, the various orientations of the density measurements of the mat, which are due to the fan-shaped oath of the rays, are converted on the basis of variously oriented double determinations in the overlaps of neighbouring units by means of computing models relying on the well known technique of digital laminography and tomosynthesis.

According to another embodiment of the invention, during testing, foreign matter such as metal pieces, lumps of glue, plastic pieces and overdense particle aggregates, is detected in the mat and corresponding electrical output signals are entered into the evaluating circuit. A device for removing a portion of the mat containing the foreign matter is controlled through the evaluating circuit. All of the foreign matter encountered in practical operation may be detected and removed together with the corresponding portion of the mat. Despite the greatest care exercised in carrying out the process, foreign matter of various kind and size are repeatedly encountered in the mats. This foreign matter includes metal pieces from the raw wood or from previous processing stages, metal and plastic parts originating from possible admixtures of waste material, solidified or cured lumps of glue from the binder applicator or overdense particle aggregates which may form at the various stages of the process. Said foreign matter form invisible overdense sites in the mat. As wood cannot be compressed beyond its bulk density of approximately 1,500 kg/m$^3$, these overdense sites in the mat cannot be compressed to reach the final thickness of the finished plate set at the hot press and their density cannot be increased. In order not to damage the hot press, it is therefore of considerable advantage if all of the foreign matter can be removed from the mat. The device for removing a portion of the mat containing foreign matter may be provided, in a manner well known in the art, with a forming belt that is divided transverse to the direction of motion thereof and may be parted to temporarily form a slot. A discharge chute into which the defective portion of mat is cast is arranged downstream of the slot. Then, the slot of the forming belt is closed again and the process is resumed.

According to another embodiment of the invention, during testing, the weight per unit area of the mat is continuously determined in kg/m³ for the entire surface of the mat from the output signals entered into the evaluating circuit by way of the evaluating circuit. The density data obtained also permit determining the weight per unit area of the entire surface of the mat. It is thus also possible to monitor the mat with regard to undesired variations in the weight per unit area occasioned by the scattering machine and to make corrections where needed.

According to another embodiment of the invention, at one longitudinal border of the mat at least an outer portion of an outer unit of an outer radiation source and of an outer line of detector elements is adjusted to a region located outside the longitudinal border of the mat. A standard body with a known weight per unit area and at least one associated outer detector element are disposed in a first part of each region located outside the longitudinal border of the mat. At least one outer detector element onto which the beam impinges directly is disposed in a second part of each region. A calibration of the associated outer unit is performed using each standard body and the output signals of the outer detector elements. At least one of the other units radiating through the mat and neighbouring every outer unit is calibrated from a respective one of the radiation sources and of the lines of the detector elements using the output signals of the outer detector elements. Accordingly, simple and reliable calibration of the units consisting of radiation source and associated detector elements is made possible. The standard body is preferably arranged on only one of the two long borders of the mat.

Other embodiments of the invention provide a convenient way to proceed for calibration. For example, according to one embodiment, all of the other units are calibrated successively or simultaneously using the output signals of the outer detector elements. Further, according to another embodiment: at least one first of the other units is calibrated using the output signals of the outer detector elements; a second of the other units is next calibrated using output signals of the line of detector elements of the first other unit; and all of the remaining other units are calibrated in an analogous manner.

It is also the object of the present invention to control the scattering machine arranged upstream. The solution to this object is achieved by the features recited in another embodiment of the resent invention. This embodiment addresses a method of testing a mat moved in one direction and made of biomass particles, more specifically of fibers and/or wood chips for manufacturing boards. On a first side of the mat, there is provided an array of detector elements extending transverse to the direction of motion of the mat. Detector elements receive the beam that originates from at least one radiation source disposed on a second side of the mat located opposite the first side thereof and that has passed through the mat. Each detector element produces electrical output signals that are proportional to the received beam and that these signals are entered into an evaluating circuit. The output signals of the detector elements are arranged in successive groups of output signals over the width of the mat. The output signals of each group, which each represent the density of a longitudinal strip of mat, are processed together in the evaluating circuit. Each thus processed group of output signals yields a controlled variable for a reaction mechanism that is associated to the corresponding longitudinal strip and takes place in a scattering machine scattering the biomass particles to form the mat. The density data which have been obtained for the entire surface of the mat may also be advantageously used to control the scattering machine arranged upstream. Each longitudinal strip may have a width ranging e.g., from 10 to 20 cm. The width of the longitudinal strips may be adjusted to the width of the reaction mechanisms in the scattering machine. Various such reaction mechanisms are known which permit to scatter the corresponding longitudinal strip of the mat so that it is more or less dense.

According to another embodiment of the invention, the evaluating circuit controls a device for removing a portion of mat the weight per unit area of which is too low, i.e., mat portions of too low a density may be removed.

Another embodiment of the invention addresses a device for testing a mat moved in one direction and made of biomass particles, more specifically of fibers and/or wood chips for manufacturing boards. On a first side of the mat, there is provided an array of detector elements extending transverse to the direction of motion of the mat. The detector elements receive the beam that originates from a second side of the mat located opposite the first side thereof and that has passed through the mat. Each detector element is adapted to produce an electrical output signal that is proportional to the received beam and that this signal is enterable into an evaluating circuit. The detector elements are arranged in a plane parallel to the mat. An array of radiation sources extending transverse to the direction of motion is provided on the second side of the mat. The radiation sources are positioned with a transversely spaced-apart relationship transverse to the direction of motion of the mat. The beam originating from every radiation source is shaped into a fan-shaped beam, a width of each fan-shaped beam extending transverse to the direction of motion of the mat. Distal ends of neighbouring fan-shaped beams are disposed in overlapping relation with one another transverse to the direction of motion of the mat. The overlay occurs over at least one thickness of the mat. One line of detector elements of the array of detector elements is radiated by each fan-shaped beam. Neighboring fan-shaped beams and the respective one of the associated lines of detector elements are longitudinally spaced a distance from each other in the direction of motion of the mat.

According to another embodiment of the invention, an aperture angle of each fan-shaped beam ranges from approximately 30°to 60°, and preferably amounts to 44°. The number of radiation sources and the evaluation of the electrical output signals obtained can be optimised in function of the type of mat that is to be tested.

According to another embodiment of the invention, all of the radiation sources are configured in the same manner and are arranged on a plane parallel to the mat. Such an arrangement provides operational and cost advantages.

These and further advantages and characteristics of the present invention will become apparent in the following description of an exemplary embodiment that is explained in more detail with reference to the drawings.

DETAILED DESCRIPTION

Figure 1:
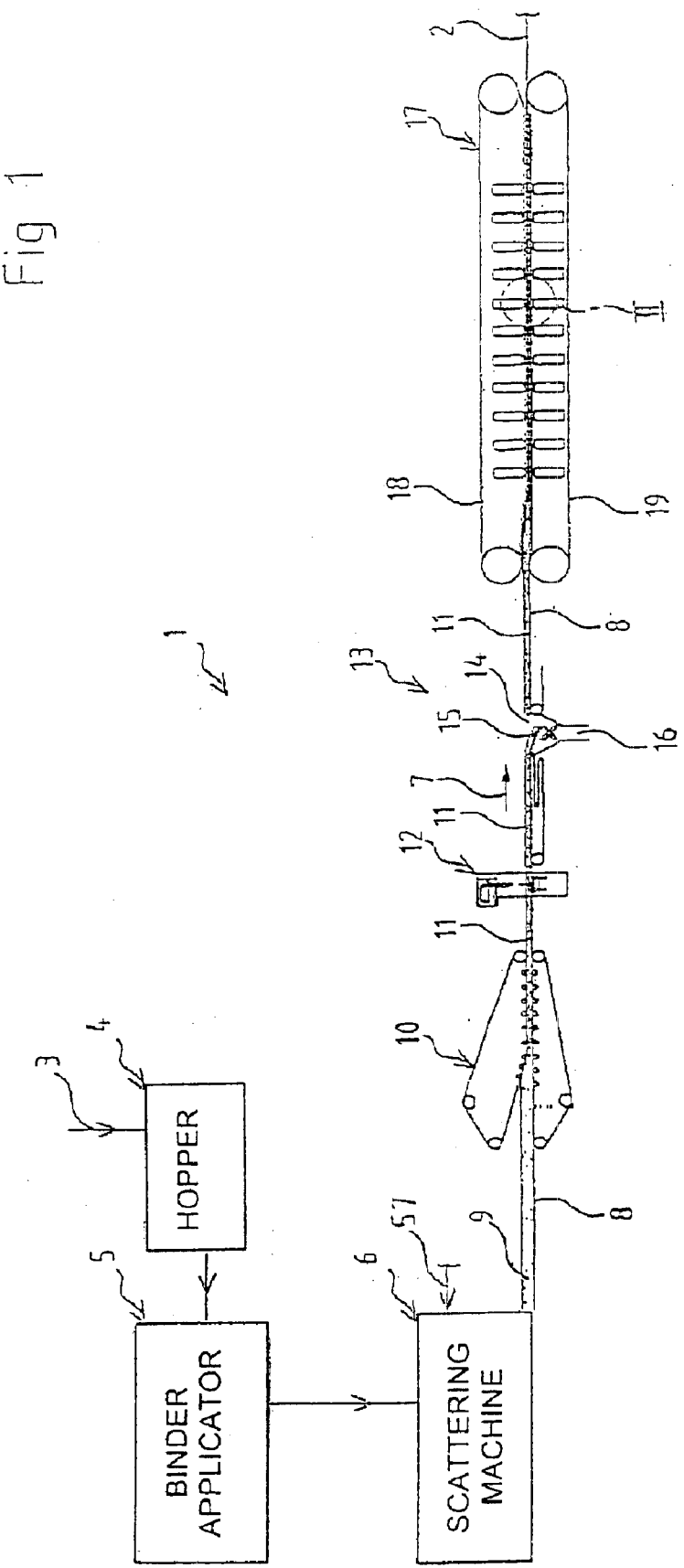
FIG. 1 is a schematic flow diagram illustrating the manufacturing of the mats and boards.

FIG. 1 schematically shows a line 1 for the continuous manufacturing of boards 2 made of biomass particles that are fed to a hopper 4 in the direction shown by an arrow 3. From hopper 4, the biomass particles, more specifically the fibers and/or wood chips, are transferred to a binder applicator 5 from where they are fed to a scattering machine 6.

In a manner well known in the art, the scattering machine 6 scatters the biomass particles on a forming belt 8 being moved in a direction of motion 7. A nonwoven sheet or mat 9 made of biomass particles is thus produced on the forming belt 8.

The mat 9 is then preferably precompressed in a continuous cold press 10. Next, the precompressed mat 11 is conveyed through a testing device 12. On the one hand, the testing device 12 tests the mat 11 for foreign matter like metal pieces, lumps of glue, plastic pieces, overdense particle aggregates and similar pieces. On the other end, the testing device permits to additionally determine the weight per unit area of the mat 11 over the entire surface thereof if necessary.

In the region of a device 13, the forming belt 8 is divided transverse to the direction of motion 7 and may be parted to form a gap 14 when the testing device 12 detects a flaw in the mat 11. A portion 15 of mat 11, in which the flaw was found, may thus be cast into a discharge chute 16. As soon as this has happened, the forming belt 8 is caused to join again and the gap 14 is closed. Thereupon, the mat 11 is transferred further in the direction of motion 7 to a continuous hot press 17. In the hot press 17, the precompressed mat 11, which is now rid of the flaws mentioned, is compressed to form the finished plate 2 by the application of pressure and heat. The thermoactive binder applied to the biomass particles inside the binder applicator 5 thereby cures and causes the particles to bond together and the finished board 2 to solidify.

Hot press 17 preferably is a conventional double band press in which the board 2 is compressed between an upper press belt 18 and a lower press belt 19. The press belts 18, 19 consist of steel bands of e.g., 2.5 mm thick that extend over the entire width of the board 2.

Figure 2:
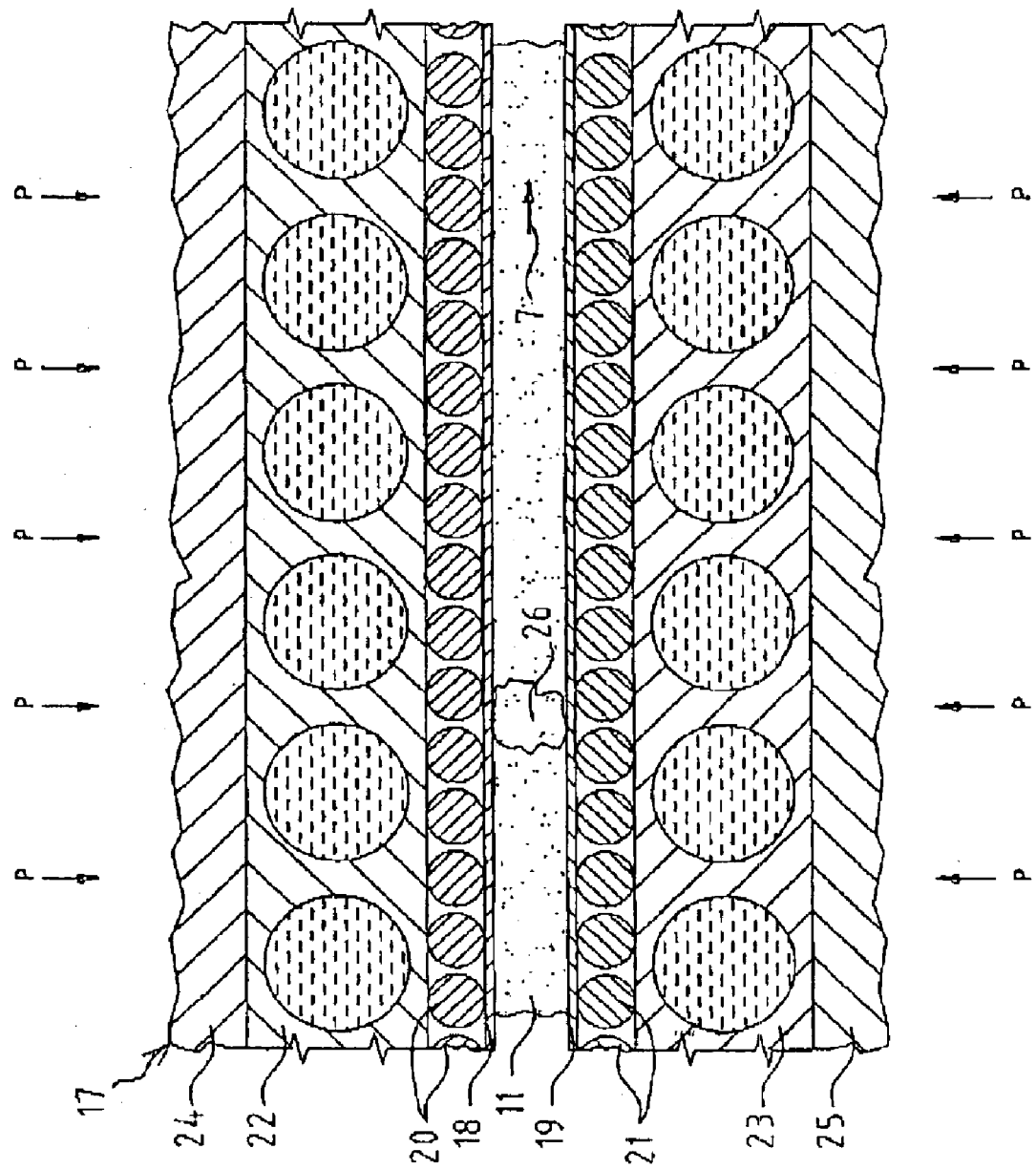
FIG. 2 is the enlarged detail II of FIG. 1.

Further details of the hot press 17 are shown in FIG. 2. The press belts 18, 19 abut on upper roller bars 20 and on lower roller bars 21 which in turn are supported by an upper heating plate 22 and a lower heating plate 23. The upper heating plate 22 abuts on a press plate 24 whereas the lower heating plate 23 rests on a press table 25. Pressing forces P are applied to the system in a manner well known in the art.

When the precompressed mat 11 according to FIG. 2 contains one or several unwanted high-density pieces of foreign matter 26 that cannot be compressed beyond the bulk density of wood, which approximately amounts to 1,500 kg/m³, said pieces of foreign matter 26 cannot be compressed to the final thickness of the finished board 2 (FIG. 1) set at the hot press 17 and the density thereof cannot be increased any further. As a matter of fact, the same applies to metallic foreign matter 26. Besides metallic foreign matter 26, foreign matter 26 in the form of lumps of glue loosening from the binder applicator system may get into the mat 11. Foreign matter in the form of metal and plastic pieces resulting from admixtures of waste material are also to be found. Further possible foreign matter 26 to be encountered are high-density fiber lumps with a high share of glue that form sometimes in the scattering machine. Such pieces of foreign matter 26 may have different sizes. In MDF boards, the pieces of foreign matter 26 may have a size of 2 to 3 mm, in OSB, the foreign matter 26 may be of a much larger size and reach up to 5 cm.

Since known hot presses 17 are isochoric, i.e., they operate by maintaining a predetermined distance between the press plate 24 and the press table 25, the press belts 18, 19 cannot avoid the foreign matter 26 and are easily damaged by the foreign matter 26. These damages may take the form of bulges, cracks or even perforations occurring in the press belts. At the worst, even the roller bars 20, 21 and the heating plates 22, 23 may become damaged. It is therefore of particular importance and a substantial object of the present invention to ensure that no unwanted foreign matter 26 is still left in the mat 11 when said precompressed mat 11 enters the hot press 17.

Figure 3:
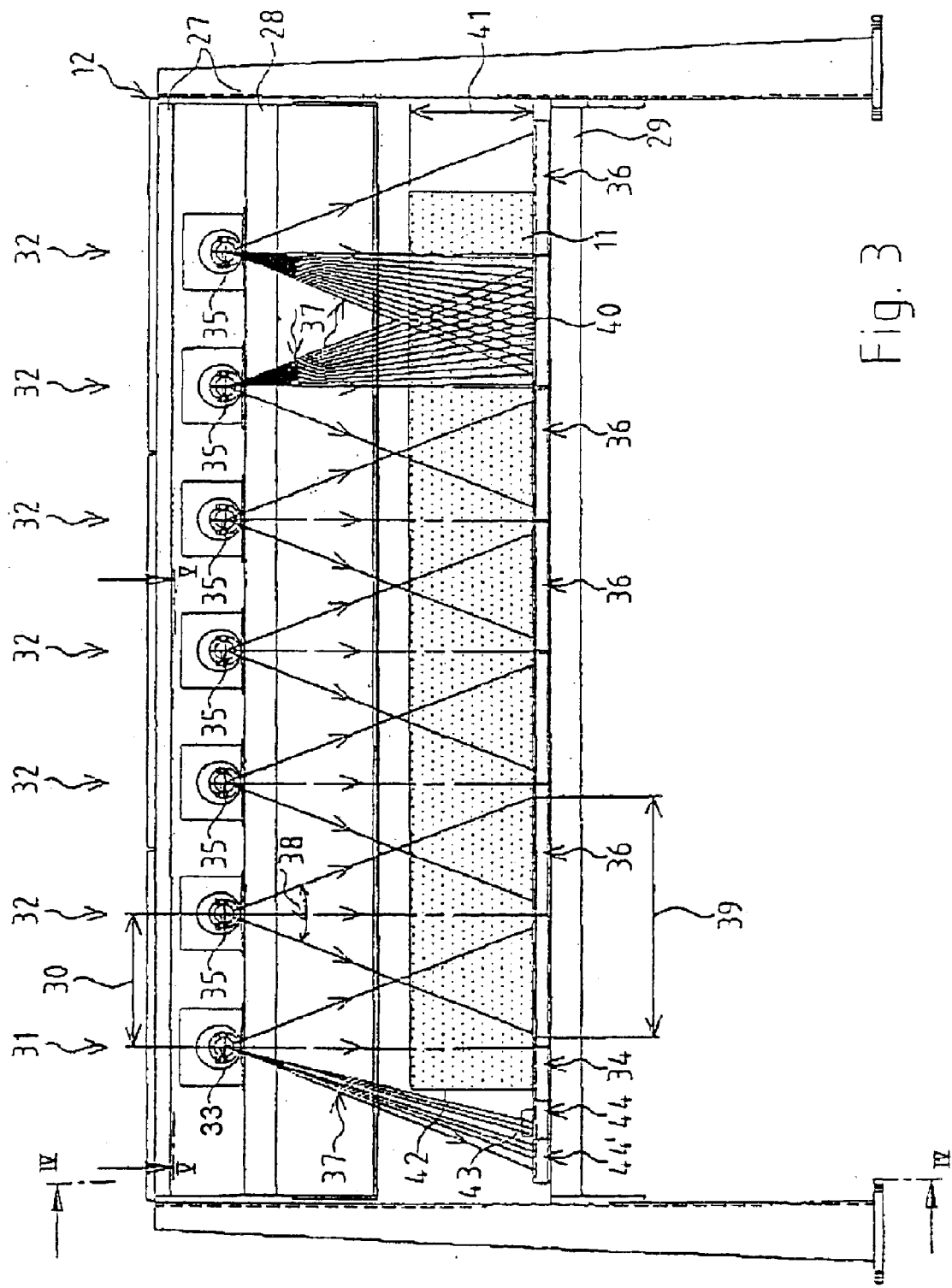
FIG. 3 is a side view of a testing device.

FIG. 3 shows details of the testing device 12. The device 12 is provided with a frame 27 having an upper tie bar 28 and a lower tie bar 29.

In FIG. 3, the direction of motion 7 (FIG. 1) is oriented normal to the plane of the drawing. An outer unit 31 and other units 32 are mounted on the tie bars 28, 29 transverse to said direction of motion 7. The outer unit 31 is provided with an outer radiation source 33 and an outer line 34 of detector elements 44, 44', 51 (FIG. 5) that extends transverse to the direction of motion 7, said detector elements being mounted on the lower tie bar 29. Each other unit 32 consists of a radiation source 35 on the upper tie bar 28 and of a line 36 of detector elements 51 (FIG. 5) that extends transverse to the direction of motion 7, said detector elements being in turn mounted on the lower tie bar 29. Each detector element 44, 44', 51 is provided with a line of e.g., 128 detector cells, i.e., pixels (not shown). The output signals may be for example periodically retrieved from the detector cells in the form of data of density values and be evaluated.

The beam emitted by each radiation source 33, 35 is formed into a fan 37 with an aperture angle 38 that ranges between 30° and 60° and preferably amounts to 44°. A width 39 of each fan-shaped beam 37 extends transverse to the direction of motion 7 of the mat 11 and is flush with the corresponding line 34, 36 of detector elements. According to FIG. 3, distal ends of neighbouring fan-shaped beams 37 are disposed in overlapping relation with one another transverse to the direction of motion 7. This is more specifically shown for the two other units 32 on the right side of FIG. 3. When the mat 11 is radiographed, a double information about the density of mat 11 is obtained for the triangular overlap 40 of neighbouring fan-shaped beams 37. Said double information may be used to calculate, in a manner to be described later on, the weight per unit area of the mat 11. It is for example advantageous when the height of the overlap 40 is at least equal to a thickness 41 of the mat 11. As a result thereof, the information about the density may be obtained for the entire width of the mat.

As shown in FIG. 3, a left portion of the fan-shaped beam 37 of the outer unit 31 is directed past a longitudinal border 42 of mat 11 and penetrates a standard body 43, the weight per unit area of which is known, that is located on the outer line 34 of detector elements 44, 44', 51. The portion of the beam, which has not penetrated through the mat 11 but through the standard body 43 only, is received by at least one outer detector element 44 (see also FIG. 5) of the outer line 34 of detector elements and is converted into electrical output signals. According to FIG. 5, said output signals are transferred via a line 45 to an evaluating circuit 46 where they are used to calibrate the outer unit 31 and the other units 32. An outer portion of the left fan-shaped beam 37 in FIG. 3 is directed past the standard body 43 and is received by at least one outer detector element 44' of the outer row 34 of detector elements. In FIG. 3, the outer detector element 44' may be arranged on the left side (as shown) or on the right side of the outer detector element 44. The portion of beam received by the outer detector element 44' is converted into reference output signals that are supplied via a line 45' (FIG. 5) to the evaluating circuit 46 and are used to calibrate the outer unit 31. All of the other units 32 may be aligned with the outer unit 31. It is also possible though to first calibrate the other unit 32 which neighbours the outer unit 31 according to outer unit 31 and to then calibrate one after the other all of the remaining other units 32 accordingly.

Figure 4:
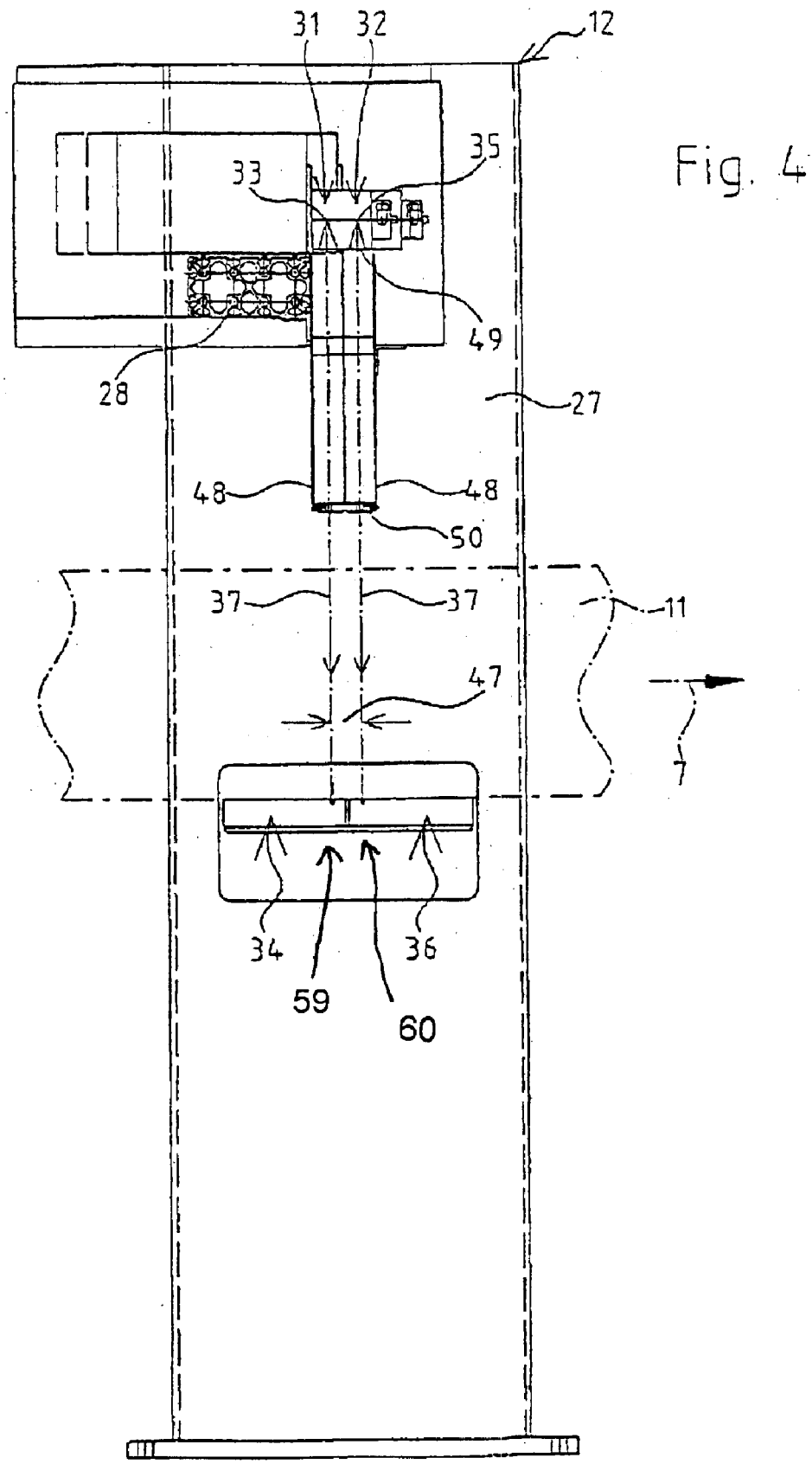
FIG. 4 is an enlarged sectional view taken along the line IV—IV of FIG. 3

According to FIG. 4, the units 31, 32 are provided in multiple rows 59, 60 such that neighbouring fan-shaped beams 37, 37 (and their associated lines 34, 36 of detector elements) are longitudinally spaced a distance 47 of e.g., 50 mm from each other in the direction of motion 7 of mat 11. As a result, the fan-shaped beams of radiation emitted by the radiation sources 35 in FIG. 3 appear to overlay in the direction of motion 7 of the mat 11.

Conventional X-ray tubes are preferably used as radiation sources 33, 35, said tubes acting in principle like point emitters. The fan-shaped beams 37 are formed by collimator ducts 48, each collimator duct 48 having an upper collimator slot 49 and a lower collimator slot 50.

Figure 5:
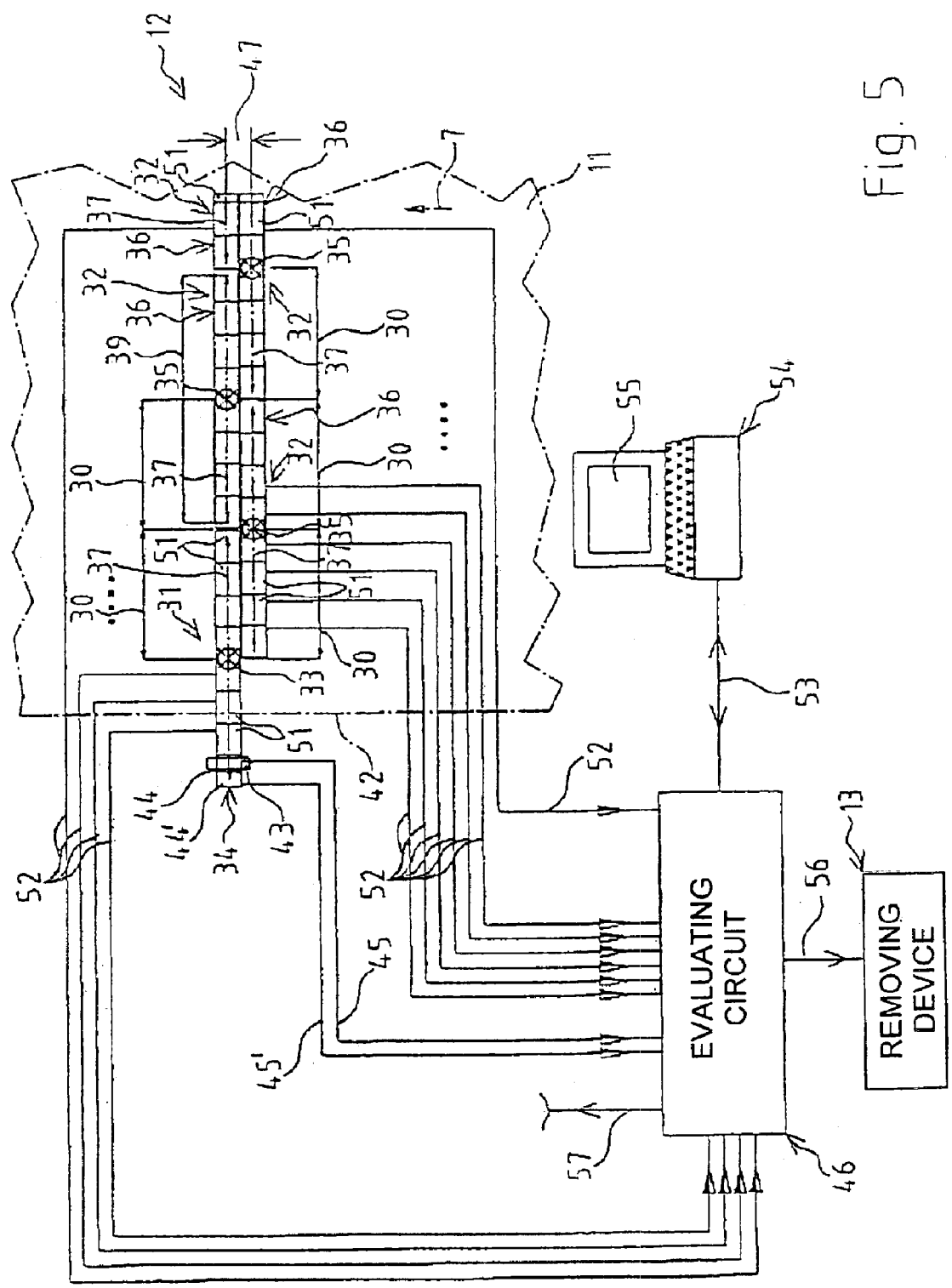
FIG. 5 is a schematic view taken along V—V of FIG. 3 with associated circuit array.

As schematically shown in FIG. 5, the outer line 34 of detector elements is provided, aside from the outer detector elements 44, with detector elements 51. The other lines 36 of detector elements also consist of such detector elements 51. Each detector element 51 is connected to the evaluating circuit 46 by way of a line 52. For the sake of simplification, FIG. 5 illustrates only some of said detector elements 51 and of the connecting lines 52 thereof. FIG. 5 also clearly shows how the fan-shaped beam 37 of each unit 31, 32 is aligned with its line 34, 36 of detector elements. In this way, the electrical output signals of all of the detector elements 44, 44', 51 are transferred to the evaluating circuit 46 where they are processed. The evaluating circuit 46 is connected to an input/output unit 54 with monitor 55.

If the testing device 12 detects foreign matter 26 (FIG. 2) in the mat 11, the evaluating circuit 46 controls via line 56 the device 13 for removing the portion 15 of mat 11 containing the foreign matter 26.

The detector elements 51 supply electrical output signals that are proportional to the density of the radiated-through mat 11. Due to the chosen linear array of lines 34, 36 of detector elements, the distances from the associated radiation source 33, 35 to the detector elements 51 vary over the length of each line 34, 36. The individual rays of each fan-shaped beam 37 further have beam paths of various lengths in the mat 11 and impinge differently onto the areas of the associated detector elements 51. However, the effects of this varying geometric situation may be compensated by simple trigonometrical conversions, the angle between the respective one of the rays of the fan-shaped beam 37 and the normal being taken into consideration.

The correction calculations suffice to detect foreign matter 26 in mat 11 as only the presence and the weight of the foreign matter are of crucial interest and not the accurate localization thereof.

To determine the weight per unit area of mat 11, a further data processing step needs to be carried out in the evaluating circuit 46, though. The weight per unit area of mat 11 is to be indicated for vertically oriented portions of mat 11. The measurements, which are oriented in different ways on account of the fan-shaped beam path, must therefore be converted to corresponding results obtained from vertical averages. The conversion is based on the double measurements from various directions in the triangular overlap 40 (FIG. 3) of neighbouring units 31, 32; 32, 32. Suitable computing models rely on the well known technique of digital laminography and tomosynthesis, the interested reader being referred to the essay of S. Gondrom and S. Schröpfer, FhG ITFP, Saarbrücken, Germany, entitled "Digital computed laminography and tomosynthesis—functional principles and industrial applications", published in NDT.net—July, 1999, vol. 4, no. 7.

In the evaluating circuit 46, the output signals of the detector elements 51 are preferably arranged in successive groups of output signals over the width of the mat 11. The electrical output signals of the detector elements 51 of each group, which each represent the density of a longitudinal strip of mat 11 oriented parallel to the direction of motion 7, are processed together in the evaluating circuit 46. Each thus processed group of output signals yields a controlled variable that is used through a line 57 (see also FIG. 1) for controlling a reaction mechanism of the scattering machine 6 that is associated to the corresponding longitudinal strip of mat 11.

The priority document here, German Patent Application DE 1 01 60 398.3 filed Dec. 10, 2001, is hereby incorporated by reference.

What is claimed is:

1. A testing apparatus for testing a mat moved in one direction and made of biomass particles, the testing apparatus comprising:

a plurality of spaced-apart radiation sources that are provided in at least two rows that extend in a direction transverse to the direction of motion of the mat on a first side of the mat; and a plurality of detector elements extending transverse to the direction of motion of the mat on a second side of the mat, wherein each row of radiation sources is offset in the direction transverse to the direction of motion of the mat with respect to an adjacent row of radiation sources such that the radiation sources are staggered.

2. The testing apparatus according to claim 1, wherein each of the radiation sources is configured to emit a fan-shaped beam of radiation having a width that extends in the direction transverse to the direction of motion of the mat.

3. The testing apparatus according to claim 2, wherein distal ends of neighboring fan-shaped beams appear to creating an overlapping region when viewed in the direction of motion of the mat.

4. The testing apparatus according to claim 3, wherein the overlapping region is created over at least one thickness of the mat.

5. The testing apparatus according to claim 2, wherein each of the detector elements is configured to receive beams of radiation that originate from the first side of the mat located opposite the second side thereof.

6. The testing apparatus according to claim 5, wherein each detector element produces one or more electrical output signals that are proportional to the received beam of radiation.

7. The testing apparatus according to claim 6, wherein the electrical signals are input into an evaluating circuit.

8. The testing apparatus according to claim 7, wherein variations of density measurements of the mat, which are due to the fan-shaped path of the beams of radiation, are resolved by means of computing models relying on digital laminography and tomosynthesis.

9. The testing apparatus according to claim 2, wherein an aperture angle of each fan-shaped beam ranges from about 30° to about 60°.

10. The testing apparatus according to claim 9, wherein the aperture angle of each fan-shaped beam is about 44°.

11. The testing apparatus according to claim 1, wherein each of the detector elements is configured to receive beams of radiation that originate from the first side of the mat located opposite the second side thereof.

12. The testing apparatus according to claim 11, wherein certain of the detector elements are configured to receive beams of radiation that pass through the mat.

13. The testing apparatus according to claim 11, wherein each detector element produces one or more electrical output signals that are proportional to the received beam of radiation.

14. The testing apparatus according to claim 13, wherein the electrical signals are input into an evaluating circuit.

15. The testing apparatus according to claim 14, wherein various distances between the radiation sources and the mat due to: (a) the fan-shaped path of the beams of radiation; (b) various beam paths through the mat; and/or (c) variously radiated surfaces of the detector elements are trigonometrically resolved by the evaluating circuit.

16. The testing apparatus according to claims 14, wherein the apparatus is configured to detect foreign matter in the mat based on the electrical signals entered into the evaluating circuit, and further comprising:
    a device that is configured to remove a portion of the mat containing the foreign matter and that is controlled by the evaluating circuit.

17. The testing apparatus according to claim 14, wherein the apparatus is continuously configured to determined the weight per unit area of the mat over the entire surface of the mat from the electrical signals entered into the evaluating circuit.

18. The testing apparatus according to claim 14, wherein the evaluating circuit controls a device for removing a portion of the mat based on the weight per unit area of the mat.

19. The testing apparatus according to claim 14, wherein the evaluating circuit controls a scattering device that feeds biomass particles into the apparatus to form the mat.

20. The testing apparatus according to claim 1, wherein the detector elements are arranged on a plane parallel to the mat.

21. The testing apparatus according to claim 20, wherein the radiation sources are arranged on a plane parallel to the mat.

22. The testing apparatus according to claim 1,
    wherein in a region located outside a longitudinal border of the mat at least an outer portion of an outer radiation source and an outer line of detector elements is adjusted,
    wherein a standard body with a known weight per unit area and at least one associated outer detector element are disposed in the region located outside the longitudinal border of the mat, and
    wherein a calibration of the outer radiation source and the outer line of detector elements is performed using the standard body and the output signals of the outer detector elements.

23. The testing apparatus according to claim 22, wherein all of the other radiation sources are calibrated successively or simultaneously using the output signals of the outer detector elements.

24. The testing apparatus according to claim 22,
    wherein a first of the other radiation sources is configured to be calibrated using the output signals of the outer detector elements, and
    wherein a second of the other radiation sources is subsequently configured to be calibrated using the output signals of the line of detector elements of the first of the other radiation sources.

25. A method for testing a mat moved in one direction and made of biomass particles, the method comprising the steps of:
    providing at least two rows of units that are arranged in a direction transverse to the direction of motion of the mat and parallel to the surface of the mat,
        wherein the at least two rows of units are arranged in two mutually parallel planes that are spaced from each other in the direction of motion of the mat by a predetermined distance,
        wherein each unit comprises on one side of the mat a radiation source and on the opposite side of the mat an associated detector element in alignment with the associated radiation source,
        wherein the radiation sources are equidistant from the mat,
        wherein the detector elements are equidistant from the mat,
        wherein in each row of units, the radiation sources are equally spaced,
        wherein the radiation sources in a first of the at least two rows are offset in the direction transverse to the direction of motion of the mat with respect to the radiation sources in a second of the at least two rows of units that is adjacent to the first of the at least two rows, and
        wherein the detector elements are linearly arranged in the at least two rows to correspond to the associated radiation sources;
    emitting, using the radiation sources, fan-shaped beams of radiation,
        wherein the fan-shaped beams of radiation have widths extending in direction transverse to the direction of motion of the mat,
        wherein each fan-shaped beam is directed toward the associated detector elements,
        wherein the distal end of the fan-shaped beam emitted by one of the radiation sources in the first of the at least two rows appears to overlap the fan-shaped beam emitted by one of the radiation sources in the second of the at least two rows, when viewed along the direction of motion of the mat,
        wherein the apparent overlap of the two fan-shaped beams defines a triangular overlapping region, and
        wherein the overlapping region is provided at least over a thickness of the mat;
    absorbing, using the detector elements, the fan-shaped beams of radiation;
    generating, using the detector elements, electric output signals that are proportional to the absorbed radiation from the radiation sources; and
    entering the electric output signals into an evaluating circuit.

26. The method according to claim 25, further comprising the step of:
  calculating trigonometrically the density of the irradiated mat while accounting for the paths of the fan-shaped beams and the surfaces of the detector elements, which are irradiated under different angles.

27. The method according to claim 25 further comprising the step of:
  determining the mass per unit of area of the irradiated mat by:
    taking into consideration both of the electric signals generated in response to the two apparently overlapping fan-shaped beams passing through each portion of the mat; and
    converting, using the evaluating circuit, the two signals through either digital laminography or tomosynthesis into values of mass per unit of area.

28. The method according to claim 27, wherein the step of determining the mass per unit of area of the irradiated mat is continuously determined by way of the evaluating circuit over the entire surface of the mat.

29. The method according to claim 25, further comprising the step of:
  identifying foreign matter in the mat based upon the electric output signals input into the evaluating circuit.

30. The method according to claim 29, wherein the foreign matter is selected from the group consisting of metal pieces, lumps of glue, plastic pieces, and overdense particle aggregates.

31. The method according to claim 29, further comprising the step of:
  removing the foreign matter from the mat.

32. The method according to claim 25,
  wherein a first radiation source and the corresponding first detector element are correspondingly positioned on both sides of a longitudinal border of the mat such that the first detector element receives radiation that passes through mat,
  wherein a standard body with a known mass per unit of area and at least one second detector element are arranged in a first portion of a region located outside the longitudinal border of the mat such that the second detector element receives radiation that does not pass through the mat but passes through the standard body, and
  wherein at least one third detector element is arranged in a second portion of the region located outside the longitudinal border of the mat such that the third detector element receives radiation that does not pass through the mat or the standard body.

33. The method according to claim 32, further comprising the step of:
  calibrating the unit comprising the second detector element using the standard body and the electric output signal of the second and third detector elements.

34. The method according to claim 33, further comprising the step of:
  calibrating the other units based on the calibration of the unit comprising the second detector element.

35. The method according to claim 34, wherein the other units are calibrated after the calibration of the unit comprising the second detector element.

36. The method according to claim 34, wherein the other units are calibrated simultaneously with the calibration of the unit comprising the second detector element.

37. The method according to claim 34, wherein the other units are calibrated successively after with the calibration of the unit comprising the second detector element.

* * * * *